United States Patent [19]

Park et al.

[11] Patent Number: 5,648,074
[45] Date of Patent: Jul. 15, 1997

[54] COMPOSITIONS AND METHODS FOR DISINFECTING CONTACT LENSES AND REDUCING PROTEINACEOUS DEPOSIT FORMATION

[75] Inventors: John Y. Park, Santa Ana; Lin Peng, Tustin; Anthony J. Dziabo, Lake Forest, all of Calif.

[73] Assignee: Allergan, Waco, Tex.

[21] Appl. No.: 353,782

[22] Filed: Dec. 12, 1994

Related U.S. Application Data

[63] Continuation-in-part of Ser. No. 277,718, Jul. 20, 1994, which is a continuation-in-part of Ser. No. 66,746, May 25, 1993, abandoned.

[51] Int. Cl.$^6$ .................................................. A61K 38/54
[52] U.S. Cl. .................. 424/94.2; 424/94.1; 424/94.63; 424/661; 435/264; 514/56; 514/54; 514/57
[58] Field of Search .................................. 424/94.1, 94.2, 424/94.63, 661; 435/264; 514/56, 54, 57

[56] References Cited

U.S. PATENT DOCUMENTS

| Re. 23,218 | 4/1950 | Levy | 162/87 |
|---|---|---|---|
| Re. 31,779 | 12/1984 | Alliger | 252/187.23 |
| Re. 32,672 | 5/1988 | Huth et al. | 435/264 |
| 2,436,134 | 2/1948 | Aston | 423/477 |
| 2,477,631 | 8/1949 | Levy et al. | 162/87 |
| 3,123,521 | 3/1964 | Wentworth | 424/615 |
| 3,278,447 | 10/1966 | McNicholas | 252/186.21 |
| 3,386,915 | 6/1968 | Rutschi | 210/754 |
| 3,450,814 | 6/1969 | Bechtold et al. | 514/54 |
| 3,563,702 | 2/1971 | Partridge | 423/478 |
| 3,585,147 | 6/1971 | Gordon | 252/187.21 |

(List continued on next page.)

FOREIGN PATENT DOCUMENTS

| 520668 | 12/1987 | Australia . |
| 1156420 | 11/1983 | Canada . |
| 0082798 | 6/1983 | European Pat. Off. . |
| 0147100 | 7/1985 | European Pat. Off. . |
| 0196075 | 1/1986 | European Pat. Off. . |
| 0168253 | 1/1986 | European Pat. Off. . |
| 0199385 | 10/1986 | European Pat. Off. . |
| 0209071 | 1/1987 | European Pat. Off. . |
| 0240315 | 10/1987 | European Pat. Off. . |
| 0279401 | 2/1988 | European Pat. Off. . |
| 0255041A1 | 5/1988 | European Pat. Off. . |
| 0278224 | 8/1988 | European Pat. Off. . |
| 0384666 | 8/1990 | European Pat. Off. . |
| 0426489 | 5/1991 | European Pat. Off. . |
| 3626082A1 | 8/1988 | Germany . |
| 1269677 | 4/1982 | United Kingdom . |
| 2094992 | 9/1982 | United Kingdom . |
| 2139260 | 11/1984 | United Kingdom . |
| 2173017A | 10/1986 | United Kingdom . |
| 2187748A | 9/1987 | United Kingdom . |
| 2187748 | 9/1987 | United Kingdom . |
| 2151039A | 7/1988 | United Kingdom . |
| WO8504107 | 9/1985 | WIPO . |
| WO8505695 | 10/1986 | WIPO . |
| WO8911878 | 12/1989 | WIPO . |
| WO9006126 | 6/1990 | WIPO . |

OTHER PUBLICATIONS

Chemical Abstracts Selects: Issue 2, 1987.
Eudragit L Data Sheet (Info L–2/e) (No pub. date).
Siu et al, "Effect of Succinylation on the Protein Quality and Urinary Excretion of Bound and Free Amino Acids", J. Agric. Food Chem 1982, 30, 1179–1183.
Communications to the Editor, "Stabilization of Microbial Proteases against Autolysis Using Acylation with Dicarboxylic Acid Anhydrides", Biotechnology and Bioengineering, vol. XXIV, pp. 483–486 (1982).
Kennedy et al, "The Oxidation of Organic Substances by Potassium Peroxymonosulfate", J Organic Chemistry 25:1901–1906 (1960).
Polymers Letters Edition, "A Study of Ozone Attach On Elastomer Surfaces By Attenuated Total Reflectance Spectroscopy", vol. 12, pp. 281–286 (1974).
Manivannan et al, "Peroxo Salts As Initiators Of Vinyl Polymerization–II" Eur. Polym. J. vol. 23, No. 4, pp. 311–313 (1987).
Evans et al, "Phase Transfer Controlled Selective Oxidation Of Diarylsulfides to Diarylsulfoxides Using Potassium Hydrogen Persulfate, Synthetic Communications", 16(10), 1207–1216 (1986).
Bloch et al, "Epoxidation of Alkenes with Potassium Hydrogen Persulfate" J. Org. Chem. 1985, 50:1544–1545.
Ball, Jr. et al., "Acylation of Egg White Proteins with Acetic Anhydride and Succinic Anhydride", Poultry Science 1982, 61:1041–1046.
W. Masschelein, "Preparation of Pure Chlorine Dioxide", vol. 6, No. 2, Jun. 1967.
I. Klotz, "Succinylation", Methods in Enzymology, vol. XI, Enzyme Structure, 1967, 576–580.
De Poorter et al, "Ozone As Oxygen Donor In The Catalytic Hydroxylation Of Saturated Hydrocarbons", Tetrahedron Letters, vol. 26, No. 32 pp. 4459–4462 (1985).
Trost et al, "Chemoselective Oxidation of Sulfides to Sulfones with Potassium Hydrogen Persulfate", Tetrahedron Letters, vol. 22, No. 14, pp. 1287–1290 (1981).

*Primary Examiner*—Jean C. Witz
*Attorney, Agent, or Firm*—Frank J. Uxa

[57] ABSTRACT

Compositions and methods for disinfecting contact lenses are disclosed. In one embodiment, the present compositions include a liquid medium containing chlorine dioxide precursor in an amount effective to form, when activated, a chlorine dioxide-containing composition including a contact lens disinfecting amount of chlorine dioxide. A polyanionic component, preferably a water soluble polyanionic component, is included in the composition in an amount effective to inhibit the formation of proteinaceous deposit material on a contact lens immersed in the chlorine dioxide-containing composition. Thus, effective contact lens disinfection is achieved while, at the same time, reducing the risk of forming proteinaceous deposit material on the contact lens during the disinfecting processing.

16 Claims, No Drawings

U.S. PATENT DOCUMENTS

| | | | |
|---|---|---|---|
| 3,591,515 | 7/1971 | Lovely | 252/186.22 |
| 3,622,479 | 11/1971 | Schneider | 210/748 |
| 3,763,006 | 10/1973 | Callerame | 205/556 |
| 3,819,828 | 6/1974 | McCoy | 424/70.4 |
| 3,910,296 | 10/1975 | Karageozian et al. | 134/2 |
| 3,912,451 | 10/1975 | Gaglia, Jr. | 422/30 |
| 3,920,810 | 11/1975 | Rankin | 424/78.04 |
| 4,011,941 | 3/1977 | Parsons | 206/5.1 |
| 4,084,747 | 4/1978 | Alliger | 422/20 |
| 4,104,190 | 8/1978 | Hartshorn | 252/187.21 |
| 4,123,376 | 10/1978 | Gray | 510/307 |
| 4,146,496 | 3/1979 | Gray | 8/111 |
| 4,202,740 | 5/1980 | Stoner et al. | 205/701 |
| 4,236,992 | 12/1980 | Themy | 204/278 |
| 4,361,471 | 11/1982 | Kosarek | 210/748 |
| 4,386,160 | 5/1983 | Branner-Jorgensen | 435/221 |
| 4,436,730 | 3/1984 | Ellis et al. | 514/57 |
| 4,456,510 | 6/1984 | Murakami | 205/556 |
| 4,459,217 | 7/1984 | Bogie | 510/117 |
| 4,496,452 | 1/1985 | Bianchi | 204/266 |
| 4,499,077 | 2/1985 | Stockel et al. | 424/661 |
| 4,557,925 | 12/1985 | Lindahl et al. | 424/482 |
| 4,568,517 | 2/1986 | Kaspar et al. | 422/30 |
| 4,614,549 | 9/1986 | Ogunbuyi et al. | 134/19 |
| 4,618,444 | 10/1986 | Hudson et al. | 8/111 |
| 4,654,208 | 3/1987 | Stockel et al. | 424/78.08 |
| 4,689,169 | 8/1987 | Mason et al. | 252/187.21 |
| 4,689,215 | 8/1987 | Ratcliff | 424/53 |
| 4,690,773 | 9/1987 | Ogunbuyi et al. | 435/264 |
| 4,731,192 | 3/1988 | Kenjo et al. | 510/113 |
| 4,767,559 | 8/1988 | Kruse et al. | 510/114 |
| 4,786,492 | 11/1988 | Ratcliff | 424/53 |
| 4,788,053 | 11/1988 | Ratcliff | 424/53 |
| 4,792,442 | 12/1988 | Ratcliff | 424/53 |
| 4,837,009 | 6/1989 | Ratcliff | 424/53 |
| 4,855,135 | 8/1989 | Ratcliff | 424/661 |
| 4,861,514 | 8/1989 | Hutchings | 510/102 |
| 4,986,990 | 1/1991 | Davidson et al. | 424/665 |
| 4,997,626 | 3/1991 | Dziabo et al. | 422/37 |
| 5,077,258 | 12/1991 | Phillips | 502/321 |
| 5,078,908 | 1/1992 | Ripley et al. | 252/187.21 |
| 5,122,598 | 6/1992 | della Valle et al. | 536/20 |
| 5,129,999 | 7/1992 | Holland et al. | 205/701 |
| 5,135,623 | 8/1992 | Dziabo et al. | 205/70 J |
| 5,145,644 | 9/1992 | Park et al. | 422/28 |
| 5,147,861 | 9/1992 | della Valle et al. | 514/54 |
| 5,152,912 | 10/1992 | Dziabo et al. | 510/112 |
| 5,185,161 | 2/1993 | Davidson et al. | 424/665 |
| 5,197,636 | 3/1993 | Mitchell et al. | 222/190 |
| 5,212,162 | 5/1993 | Missel et al. | 514/54 |
| 5,229,128 | 7/1993 | Haddad et al. | 424/427 |
| 5,264,460 | 11/1993 | Jakobson et al. | 514/786 |
| 5,279,673 | 1/1994 | Dziabo et al. | 134/26 |
| 5,300,296 | 4/1994 | Holly et al. | 424/427 |
| 5,302,399 | 4/1994 | Otagiri et al. | 424/493 |
| 5,336,434 | 8/1994 | Park et al. | 252/187.21 |
| 5,338,480 | 8/1994 | Dziabo et al. | 252/187.21 |
| 5,382,599 | 1/1995 | Rupp et al. | 514/547 |

COMPOSITIONS AND METHODS FOR DISINFECTING CONTACT LENSES AND REDUCING PROTEINACEOUS DEPOSIT FORMATION

RELATED APPLICATIONS

This application is a continuation-in-part of application Ser. No. 08/277,718, filed Jul. 20, 1994, which, in turn, is a continuation-in-part of application Ser. No. 08/066,746, now abandoned, filed May 25, 1993, each of which applications is incorporated in its entirety herein by reference.

BACKGROUND OF THE INVENTION

This invention relates to compositions and methods useful in disinfecting contact lenses. More particularly, the invention relates to compositions and methods in which contact lenses are disinfected using a composition containing chlorine dioxide and a polyanionic component effective to inhibit the formation of proteinaceous deposit material on the contact lens being disinfected.

The use of chlorine dioxide dissolved in an aqueous liquid medium to disinfect contact lenses has previously been suggested. Although chlorine dioxide is very effective in disinfecting contact lenses, the tendency of the chlorine dioxide to combine with proteins, for example, lysozyme, present on or in the contact lens has caused some concern. The combination of such contact lens associated proteins and chlorine dioxide may result in the formation of proteinaceous deposits on the lenses, which may have some effect on the wearability of such lenses.

Park et al U.S. Pat. No. 5,336,434 and Dziabo et al U.S. Pat. No. 5,338,480 disclose contact lens disinfecting using chlorine dioxide in which delayed release components are used to delay the release of chlorine dioxide activators, chlorine dioxide destroying components and/or cleaning enzyme components. Various delayed release components are disclosed, for example, soluble cellulose ethers such as methylcellulose, methylhydroxpropylcellulose, methylhydroxyethylcellulose, hydroxypropylcellulose, hydroxyethylcellulose and sodium carboxymethylcelluloses; cellulose esters such as cellulose acetate phthalate and hydroxypropylmethyl-cellulose phthalate; polymers derived from at least one of acrylic acid, acrylic acid esters, methacrylic acid and methacrylic acid esters such as methacrylic acid-methyl methacrylate copolymer (for example, that sold by Rohm Pharma under the trademark Eudragit L 100) and methacrylic acid-ethyl acrylate copolymers (for example, that sold by Rohm Pharma under the trademark Eudragit L 30D); polymers derived from methyl vinyl ether and maleic acid anhydride; polyvinylpyrrolidone; polyvinyl alcohols and the like and mixtures thereof. However, neither of these patents discloses that such delayed release components are effective to delay or prevent proteinaceous deposit formation on the contact lens being disinfected.

It would be advantageous to provide a contact lens disinfection system which takes advantage of the antimicrobial properties of chlorine dioxide while, at the same time, reduces or even eliminates the risk of chlorine dioxide interacting with proteins associated with the contact lens to disadvantageously produce proteinaceous deposit material on the disinfected contact lens.

SUMMARY OF THE INVENTION

New compositions, and methods for use thereof, which include a combination of chlorine dioxide and a component effective to inhibit, for example, delay or prevent, the formation of proteinaceous deposit material on contact lenses contacted with such chlorine dioxide-containing compositions have been discovered. Thus, in accordance with the present invention, the outstanding contact lens disinfecting ability of chlorine dioxide is utilized while, at the same time, inhibiting the disadvantageous formation of proteinaceous deposit material on the contact lens being disinfected. The present compositions are straightforward, easy and inexpensive to produce and use and provide outstanding benefits. Because the present inhibitor components are preferably water soluble, the present compositions can be utilized in very straightforward methods for disinfecting contact lenses. No additional steps, for example, rubbing and/or rinsing the contact lens free of proteins prior to placing the lens into a chlorine dioxide-containing composition for disinfection, are needed in order to achieve the substantial benefits of the present invention. Thus, user compliance is very easily obtained. In short, the present methods provide for the use of highly effective and advantageous chlorine dioxide to disinfect contact lenses while reducing, or even substantially eliminating, the disadvantageous formation of proteinaceous deposit material on the contact lens during disinfection.

In one broad aspect of the present invention, compositions comprising chlorine dioxide precursor and a polyanionic component are provided. The chlorine dioxide precursor is present in an amount effective to form, when activated in a liquid medium, a chlorine dioxide-containing composition including a contact lens disinfecting amount of chlorine dioxide. The polyanionic component, which preferably is included in a liquid medium containing the chlorine dioxide precursor, is present in an amount effective to inhibit the formation of proteinaceous deposit material on a contact lens immersed in the chlorine dioxide-containing composition. The polyanionic component and any precursor thereof preferably do not act as a delayed release component, that is do not act to substantially (for a controlled or substantially predetermined period of time) delay the release of another component in the chlorine dioxide-containing composition and any liquid-containing precursor thereof. In other words, the present polyanionic components are effective to inhibit proteinaceous deposit formation on contact lenses being disinfected by chlorine dioxide and preferably are not employed, in the present invention, as delayed release components.

The liquid medium preferably comprises water, and the chlorine dioxide precursor and the polyanionic component are preferably water soluble. The polyanionic component is preferably effective to inhibit the formation of proteinaceous deposit material on a contact lens immersed in the chlorine dioxide-containing composition relative to the formation of proteinaceous deposit material on a contact lens immersed in a similar chlorine dioxide-containing composition without the polyanionic component.

In one embodiment, the contact lens proteinaceous deposit material formed in a chlorine dioxide disinfection system including the present polyanionic component is easier to effectively remove relative to deposit material formed in a substantially similar chlorine dioxide disinfection system without the polyanionic component. For example, a conventional cleaning enzyme component (conventionally used to clean contact lenses) is often effective to remove proteinaceous deposits from a contact lens disinfected in a chlorine dioxide-polyanionic component-containing composition. In contrast, such cleaning enzyme component often is relatively, or even substantially, ineffective to remove proteinaceous deposits from contact lenses disinfected with chlorine dioxide-containing compositions without polyanionic components.

As used herein, the term "polyanionic component" refers to a chemical entity, for example, an ionically charged species, such as an ionically charged polymeric material, which includes more than one discrete anionic charge, that is multiple discrete anionic charges. Preferably, the polyanionic component is selected from the group consisting of polymeric materials having multiple anionic charges and mixtures thereof. Particularly useful anionic components are selected from anionic cellulose derivatives, anionic polymers derived from acrylic acid (meaning to include polymers from acrylic acid, acrylates and the like and mixtures thereof), anionic polymers derived from methacrylic acid (meaning to include polymers from methacrylic acid, methacrylates, and the like and mixtures thereof), anionic polymers derived from alginic acid (meaning to include alginic acid, alginates, and the like and mixtures thereof), anionic polymers of amino acids (meaning to include polymers of amino acids, amino acid salts, and the like and mixtures thereof), and the like and mixtures thereof. Very useful polyanionic components are those selected from anionic cellulose derivatives and mixtures thereof, especially carboxymethylcelluloses.

The polyanionic component is preferably sufficiently anionic to interact with lysozyme, which is cationically charged, and is present with the contact lens immersed in the chlorine dioxide-containing composition. This interaction is preferably sufficient to render the lysozyme soluble in the chlorine dioxide-containing composition. Without wishing to limit the invention to any particular theory of operation, it is believed that with the lysozyme soluble in the chlorine dioxide-containing composition, the lysozyme is removed or separated from the surface of the contact lens, thereby, at least to some extent, contributing to the inhibition of proteinaceous deposit formation on the contact lens being disinfected.

Methods for disinfecting contact lenses are included within the scope of the present invention. In one embodiment, the present methods comprise contacting a contact lens with a liquid medium containing chlorine dioxide in an amount effective to disinfect a contact lens. The liquid medium includes a polyanionic component in an amount effective to inhibit the formation of proteinaceous deposit material on the contact lens.

These and other aspects of the present invention will become apparent hereinafter, particularly when considered in conjunction with the following detailed description, examples and claims.

DETAILED DESCRIPTION OF THE INVENTION

The present compositions are applicable for disinfecting, and preferably cleaning, all types of contact lenses. These contact lenses, for example, conventional hard contact lenses and soft contact lenses, may be made of any material or combination of materials and may have any suitable configuration. Since soft contact lenses are particularly susceptible to being associated with lysozyme, for example, while being worn in the eye, the present invention is particularly useful in disinfecting such soft contact lenses.

One important feature of the present invention is the use of chlorine dioxide precursors. Among the chlorine dioxide precursors suitable for use are those which are adapted to provide for controlled formation of contact lenses disinfecting amounts of chlorine dioxide. Thus, such precursors allow the chlorine dioxide disinfectant to be shipped and stored with minimum loss of disinfecting power. Chlorine dioxide is formed when needed and wanted, in a liquid medium contacting a lens to be disinfected. As used herein, a disinfecting amount of chlorine dioxide is such amount as will reduce the microbial burden or load by one log order in 3 hours or less, preferably in 1 hour or less, and more preferably in 10 minutes or less. Of course, the amount of chlorine dioxide employed should not cause any substantial damage to the lens.

Specific examples of chlorine dioxide precursors include stabilized chlorine dioxide (SCD), metal chlorites, such as alkali metal and alkaline earth metal chlorites, and the like and mixtures thereof. Technical grade sodium chlorite is a very useful chlorine dioxide precursor. Chlorine dioxide-containing complexes, such as complexes of chlorine dioxide with carbonate, chlorine dioxide with bicarbonate and mixtures thereof are also included as chlorine dioxide precursors. The exact chemical composition of many chlorine dioxide precursors, for example, SCD and the chlorine dioxide complexes, is not completely understood. The manufacture or production of certain chlorine dioxide precursors is described in McNicholas U.S. Pat. No. 3,278,447, which is incorporated in its entirety herein by reference. Specific examples of useful SCD products include that sold under the trademark Dura Klor by Rio Linda Chemical Company, Inc., and that sold under the trademark Anthium Dioxide by International Dioxide, Inc. An especially useful SCD is a product sold under the trademark Purogene® by Bio-Cide International, Inc.

The chlorine dioxide precursor may be included in a liquid medium at a predetermined concentration, e.g., to provide a disinfecting amount of chlorine dioxide in the presence of an activator component or components. For example, a chlorine dioxide precursor may be included in a liquid medium at a concentration chosen to provide a disinfecting amount of chlorine dioxide in response to at least one factor other than the presence of the lens to be disinfected. Preferably, the liquid medium includes sufficient chlorine dioxide precursor so as to have a potential of producing chlorine dioxide in the range of about 0.2 ppm to about 3%, more preferably about 0.5 ppm to about 0.05% or about 0.1% (weight chlorine dioxide/volume of liquid medium).

Any suitable polyanionic component may be employed in accordance with the present invention provided that it functions as described herein and has no substantial detrimental effect on the contact lens being disinfected or on the wearer of the disinfected contact lens. The polyanionic component is preferably ophthalmically acceptable at the concentrations used to inhibit proteinaceous deposit material on contact lenses. The polyanionic component preferably includes three (3) or more anionic (or negative) charges. In the event that the polyanionic component is a polymeric material, it is preferred that each of the repeating units of the polymeric material include a discrete anionic charge. Particularly useful anionic components are those which are water soluble, for example, soluble at the concentrations used in the presently useful liquid aqueous media, such as a liquid aqueous medium containing the polyanionic component and chlorine dioxide precursor and/or chlorine dioxide.

As noted above, the polyanionic component is preferably sufficiently anionic to interact with tear proteins, such as lysozyme, which are cationically charged. Such interaction is desirable to solubilize such tear proteins and/or to maintain such tear proteins soluble in the liquid disinfecting medium. Such soluble tear proteins are believed to be less likely to form proteinaceous deposit materials on the contact lens being disinfected.

A particularly useful class of polyanionic components are one or more polymeric materials having multiple anionic charges. Examples include:

metal carboxymethylcelluloses metal carboxymethylhydroxyethylcelluloses metal carboxymethylstarchs metal carboxymethylhydroxyethylstarchs hydrolyzed polyacrylamides and polyacrylonitriles heparin homopolymers and copolymers of one or more of:

acrylic and methacrylic acids metal acrylates and methacrylates alginic acid metal alginates vinylsulfonic acid metal vinylsulfonate amino acids, such as aspartic acid, glutamic acid and the like metal salts of amino acids p-styrenesulfonic acid metal p-styrenesulfonate 2-methacryloyloxyethylsulfonic acids metal 2-methacryloyloxethylsulfonates 3-methacryloyloxy-2-hydroxypropylsulonic acids metal 3-methacryloyloxy-2-hydroxypropylsulfonates 2-acrylamido-2-methylpropanesulfonic acids metal 2-acrylamido-2-methylpropanesulfonates allylsulfonic acid metal allylsulfonate and the like.

The present polyanionic components often can exist in the un-ionized state, for example, in the solid state, in combination with a companion or counter ion, in particular a plurality of discrete cations equal in number to the number of discrete anionic charges so that the un-ionized polyanionic component is electrically neutral. For example, the present un-ionized polyanionic components may be present in the acid form and/or in combination with one or more metals. Since the polyanionic components are preferably ophthalmically acceptable, it is preferred that the metal associated with the un-ionized polyanionic component be ophthalmically acceptable in the concentrations used. Particularly useful metals include the alkali metals, the alkaline earth metals, for example, calcium and magnesium, and mixtures thereof. Sodium is very useful to provide the counter ion in the un-ionized polyanionic component. Polyanionic components which, in the un-ionized states, are combined with cations other than $H^+$ and metal cations can be employed in the present invention.

Particularly useful polyanionic components are selected from anionic cellulose derivatives, anionic polymers derived from acrylic acid (meaning to include polymers from acrylic acid, acrylates and the like and mixtures thereof), anionic polymers derived from methacrylic acid (meaning to include polymers from methacrylic acid, methacrylates, and the like and mixtures thereof), anionic polymers derived from alginic acid (meaning to include alginic acid, alginates, and the like and mixtures thereof), anionic polymers derived from amino acids (meaning to include amino acids, amino acid salts, and the like and mixtures thereof) and mixtures thereof. Very useful polyanionic components are those selected from anionic cellulose derivatives and mixtures thereof, especially carboxymethylcelluloses.

The amount of polyanionic component employed is that effective to inhibit the formation of proteinaceous deposit material on a contact lens being disinfected, as described herein. The specific amount of such component used is not critical to the present invention provided that it functions as a deposit formation inhibitor, as described herein. In addition, the amount of polyanionic component employed depends on a number of factors, for example, the specific polyanionic component being employed, the chlorine dioxide concentration being employed, the concentration of tear proteins, for example, lysozyme, present and the degree of deposit formation inhibition desired. In addition, excessive amounts of polyanionic component are preferably to be avoided since this may be wasteful and unnecessary and may have an adverse impact on the wearer of the disinfected contact lens. Preferably, the polyanionic component is present in an amount of at least about 0.01% (w/v) or at least about 0.05% (w/v) to about 5% (w/v) or about 2% (w/v) or about 1% (w/v), based on the volume of the liquid disinfecting medium or liquid precursor thereof.

Many of the materials useful as polyanionic components in the present invention have previously been used as delayed release components. Therefore, it is important to note that the ability of a material to act to inhibit proteinaceous deposit material formation on a contact lens being disinfected is substantially different from and independent of the ability of a material to act as a delayed release component. Preferably, in the present compositions and methods, the polyanionic components and precursors thereof (for example, the polyanionic components in un-ionized (e.g. solid) forms do not act as delayed release components for any other components in the chlorine dioxide-containing compositions and any liquid-containing precursors thereof.

In one embodiment, the present polyanionic components are combined with chlorine dioxide precursor in one or more solid particles, for example, prior to use. To illustrate, a mixture containing a polyanionic component and chlorine dioxide precursor can be formed into a suitably sized and configured pill or tablet, for example, using conventional techniques. When it is desired to disinfect a contact lens, the lens is placed into a liquid medium, e.g., buffered saline, together with the pill or tablet, which dissolves into the liquid medium. The chlorine dioxide precursor is activated, for example, by the presence of a platinum group metal, to form a contact lens disinfecting amount of chlorine dioxide. The contact lens is disinfected. In addition, the polyanionic component is effective to inhibit proteinaceous deposit material on the contact lens before, during and after disinfection. The disinfected lens can be removed from the liquid medium and placed directly in the eye for safe and comfortable wear. Alternately, the disinfected lens can be removed from the liquid medium, rinsed free of the liquid medium using a buffered saline and then placed in the eye for safe and comfortable wear.

The liquid media useful in the present invention are selected to have no substantial detrimental effect on the lens being treated or cared for and to allow or even facilitate the present lens treatment or treatments. The liquid media are preferably aqueous-based. A particularly useful aqueous liquid medium is that derived from saline, for example, a conventional saline solution or a conventional buffered saline solution. During the composition-contact lens contacting step or steps, for example, during the contact lens disinfecting contacting, the aqueous liquid medium preferably has a pH in the range of about 6 to about 10, more preferably about 6 to about 8, and still more preferably about 7.5. The liquid medium preferably has a ophthalmically acceptable tonicity level, for example, of at least about 200 mOsmol/kg, more preferably in the range of about 200 to about 400 mOsmol/kg.

The liquid media containing the chlorine dioxide precursors (and/or chlorine dioxide) and polyanionic components preferably have viscosities of less than 50 centipoise (cps) at 25° C., and more preferably less than about 25 or about 20 cps at 25° C.

The present compositions may further comprise an activator component in an amount effective when released in the liquid medium to promote or to effect formation of chlorine dioxide, for example, a contact lens disinfecting amount of chlorine dioxide, from the chlorine dioxide precursor in the liquid medium.

Any suitable activator component may be employed to promote or to effect the generation of chlorine dioxide from the presently useful chlorine dioxide precursors. Examples include, acidic materials to increase the acidity of the liquid medium, transition metal components, oxygen-releasing components, organic acid anhydrides, chlorine dioxide reducing components and the like. In addition, an electrical current can be passed through a chlorine dioxide precursor-containing liquid medium to effect formation of a contact lens disinfecting amount of chlorine dioxide.

At mildly acidic conditions, in particular at a pH of less than about 6 and especially in the range of about 3 to about 5, the production of chlorine dioxide is effected from the chlorine dioxide precursors. Any suitable acidic component may be employed as the activator component. The primary criteria for such acidic component is that it have the ability to increase the acidity of the liquid medium containing chlorine dioxide precursor sufficiently to effect formation of chlorine dioxide from such chlorine dioxide precursor, and preferably sufficiently to effect formation of contact lens disinfecting amounts of chlorine dioxide from the presently useful chlorine dioxide precursors. Such acidic components should also have no substantial detrimental effect on the lens to be disinfected.

Examples of the presently useful acidic components include mineral acids and mixtures thereof. The mineral acids include, for example, nitric acid, sulfuric acid, hydrogen halides, phosphoric acid and the like. The carboxylic acids include both mono- and poly-, e.g., di-, tri- and the like, carboxylic acids, and preferably include 1 to about 10 carbon atoms per molecule. One or more non-hydrocarbonaceous groups, e.g., hydroxy groups, halide groups and the like, may be appended to the carboxylic acid. If an acid salt is employed, it is preferred that the salt be an alkali or alkaline earth metal salt, more preferably an alkali metal salt. A particularly useful group of acidic components is selected from alkali metal hydrogen phosphates, citric acid, lactic acid, tartaric acid and mixtures thereof.

During chlorine dioxide generation using an acidic component, it is preferred that the liquid aqueous medium have a pH of about 6 or less, in particular in the range of about 3 to about 5. The amount of acidic component employed is preferably sufficient to provide the precursor-containing liquid medium with the desired pH.

A more detailed description of the use of an acidic component to effect the generation of chlorine dioxide is set forth in Dziabo et al U.S. Pat. No. 5,152,912 which is incorporated in its entirety herein by reference.

Any transition metal component capable of effecting the formation of chlorine dioxide from a chlorine dioxide precursor in an aqueous liquid medium, preferably at a pH between about 6 and about 10, or possibly higher, may be employed as the activator component. The primary criteria for such transition metal component is that it have the ability to effect formation of chlorine dioxide from a chlorine dioxide precursor. Such metal component should also have no substantial detrimental effect on the lens to be disinfected. In certain embodiments, the metal component promotes the formation of chlorine dioxide in a liquid medium containing the contact lens to be disinfected. In these embodiments, it is preferred that the metal component be such as to remain effective after repeated exposure to tear components, for example, lysozyme, which are often present on contact lenses from the eye.

It is preferred that the metal component be present as a solid. In certain embodiments, solid metals can be easily and conveniently introduced into or removed from the chlorine dioxide precursor-containing liquid medium, as desired. Also a solid metal component can be readily separated from the solution for repeated use in disinfecting lenses. The metal component may be immobilized, or maintained substantially stationary, relative to the precursor-containing medium. The metal component may be positioned to contact the precursor-containing medium as the liquid medium is introduced into the container in which the contact lens is to be disinfected.

The particular metals of interest herein are the transition metals and mixtures thereof, in particular from Group III metals, Group IV metals, Group V metals, Group VI metals, Group VII metals, Group VIII metals and mixtures thereof.

Because of their high degree of effectiveness, platinum group metals and mixtures thereof, and especially platinum or palladium, are particularly useful. The platinum group metals include platinum, palladium, iridium, ruthenium, rhodium and osmium.

The metal component or components may be present in the metallic from and/or in a combined form as part of an organic or inorganic compound or complex.

The amount of metal component needed to practice this invention is to be viewed in terms of what quantity or surface area is useful to generate a particular concentration of chlorine dioxide in a given time and in light of the amount of precursor present in solution.

A more detailed description of the use of a transition metal component to effect the generation of chlorine dioxide is set forth in Ripley et al U.S. Pat. No. 5,078,908 which is incorporated in its entirety herein by reference.

Oxygen-releasing components useful as activator components in the present invention include both inorganic and organic peroxy compounds.

In one embodiment, the oxygen-releasing components which may be used in the present invention are water soluble inorganic salts such as, for example, the sodium, potassium, calcium, magnesium, lithium and ammonium salts of oxygen-releasing sulfur compounds, such as, for example, the perthiosulfates ($S_2O_5^{-1}$), the persulfates ($SO_5^{-2}$), the peroxysulfates, such as the peroxymonosulfates ($HSO_5^{-1}$) and the peroxydisulfates ($S_2O_8^{-2}$), and mixtures thereof.

A particularly preferred oxygen-releasing component is potassium peroxymonosulfate ($KHSO_5$) and the preferred form of this component is the triple salt which is a combination of potassium peroxymonosulfate ($KHSO_5$), potassium hydrogen sulfate ($KHSO_4$) and potassium sulfate ($K_2SO_4$). This composition is an acidic, water soluble, oxygen releasing powder which is odorless, white, granular, stable and free flowing. Other alkali metal, e.g., sodium, and ammonium salts are also useful.

Among useful organic peroxy compounds are the aliphatic and aromatic percarboxylic acids based on the radical

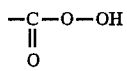

Organic peroxy compounds are preferably the aliphatic or aromatic percarboxylic acids and their alkali metal and ammonium salts. Examples of the aliphatic peracids include peracetic acid, perpropionic acid, up to perlauric acid. The preferred peracids are aromatic such as perbenzoic acid and nuclear substituted perbenzoic acids, especially those having melting points above 50° C. especially preferred is p-methoxyperbenzoic acid.

The amount of oxygen-releasing component employed should be such as to be effective to effect formation of a lens disinfecting amount of chlorine dioxide in a chlorine dioxide precursor-containing liquid medium in which the oxygen-releasing component is released. The oxygen-releasing component is preferably present, for example, during the disinfecting containing, in an amount in the range of about 0.01 mole or less to about 1 mole or more per mole of potential chlorine dioxide present as chlorine dioxide precursor in the liquid medium. Particularly useful results are achieved using oxygen releasing component in the range of about 0.01 mole to about 0.1 mole per mole of potential chlorine dioxide present as chlorine dioxide precursor in the liquid medium.

In one embodiment, the activator component comprises an organic acid anhydride component in an amount sufficient to effect formation of chlorine dioxide from the precursor.

Any suitable organic acid anhydride component may be employed. The primary criteria for such component is that it have the ability to effect formation or generation of chlorine dioxide, preferably contact lens disinfecting amount of chlorine dioxide, from chlorine dioxide precursor in a liquid medium. Such organic acid anhydride components should also have no substantial detrimental effect on the lens to be disinfected.

Examples useful organic acid anhydride components include succinic anhydride, glutaric anhydride, maleic anhydride and the like and mixtures thereof. The organic acid anhydride or anhydrides are preferably present during the disinfecting contacting in an amount in the range of about 0.01 mole or less to about 1 mole or more per mole of potential chlorine dioxide present as chlorine dioxide precursor in the liquid medium.

Any suitable chlorine dioxide reducing component may be used as an activator component in the present invention, provided that it functions as described herein and has no substantial detrimental effect, for example, on the lens being treated or on the human wearing the treated lens. Examples of useful chlorine dioxide reducing components include, but are not limited to, sulfur-containing components, such as SH (group)—containing water soluble lower alcohols, dithiothreitol, bisulfites, thio urea, beta-mercaptoethanol, 2-mercaptopropionic acid, 2-mercapto-propionylglycine,2-mercaptoethylamine hydrochloride,dithioerythritol, sulfites, pyrosulfites, thiosulfates, dithionites, glutathione and the like; N-acetylcysteine; acetylcysteine; cysteine hydrochloride ethyl ester; homocysteine; carbamoylcysteine; cysteine; cysteine hydrochloride; cysteinyl glycine; and the like and mixtures thereof. A particularly useful chlorine dioxide reducing component is selected from thiosulfates, for example, alkali metal thiosulfates, hydrogen thiosulfate and mixtures thereof.

The amount of chlorine dioxide reducing component employed should be such as to be effective to effect formation of chlorine dioxide, for example, a contact lens disinfecting amount of chlorine dioxide, in a chlorine dioxide precursor-containing liquid medium in which the chlorine in which the chlorine dioxide reducing component is released. The chlorine dioxide reducing component is preferably present, for example, during contact lens disinfecting contacting, in an amount less than that amount effective to reduce all the potential chlorine dioxide formable from the chlorine dioxide precursor in the liquid medium. The chlorine dioxide reducing component may be present in an amount in the range of about 0.01 mole or less to about 0.5 mole or more per mole of potential chlorine dioxide present as chlorine dioxide precursor in the liquid medium. Particularly useful results are achieved using amounts of chlorine dioxide reducing component in the range of about 0.01 mole to about 0.1 mole per mole of potential chlorine dioxide present as chlorine dioxide precursor in the liquid medium.

The present compositions preferably include (1) a surfactant component in an amount effective to remove deposit material from a contact lens and/or (2) an enzyme component in an amount effective to remove deposit material from a contact lens.

The deposit material to be removed may be formed in-the-eye while the contact lens is being worn and/or during the disinfecting processing. Thus, although the polyanionic components are effective to inhibit the formation of proteinaceous deposit material on a contact lens being disinfected, some such deposit material may be formed during the disinfecting with chlorine dioxide. Even if such deposit material is formed, the presence of the polyanionic components results in deposit material which is more easily removed, for example, by conventional cleaning enzymes and/or surfactants, than is the deposit material which is formed on contact lenses disinfected in chlorine dioxide-containing compositions without the polyanionic components. The formation of reduced amounts of proteinaceous deposit material and/or more easily removed proteinaceous deposit material on contact lens during disinfecting are important advantages of the present invention.

Among the types of deposit material that form on contact lenses, for example, during normal use in-the-eye, are proteinaceous deposit material, mucin-based deposit material, lipid-based deposit material and carbohydrate-based deposit material. One or more types of deposit material may be present on a single contact lens.

In one embodiment, the present compositions further include a surfactant component in an amount effective to at least facilitate the cleaning or removing of deposit material from contact lens immersed in, or contact with, the composition or the chlorine dioxide-containing composition derived therefrom. Preferably, the surfactant components used are stable in the present compositions.

In a particularly useful embodiment, the surfactant component has enhanced stability in the present compositions relative to an ethylene oxide, propylene oxide block copolymer having substantially the same contact lens cleaning efficacy as the surfactant component being employed. That is, the amount of surfactant component employed is more stable than an amount of an ethylene oxide, propylene oxide block copolymer having substantially the same contact lens cleaning efficacy as the amount of the surfactant component being employed. The surfactant component employed is preferably other than an ethylene oxide, propylene oxide block copolymer, since such block copolymers have been found to be somewhat unstable, for example, after storing the present compositions including such surfactants for relatively long periods of time.

Particularly useful surfactant components are selected from sulfates, sulfonates, alkyl polyglucosides and mixtures thereof. A number of such surfactant components are well known and are commercially available.

Specific examples of useful sulfate-containing surfactant components include alkyl sulfate salts of alkali metals and alkaline earth metals. The alkyl groups of such salts preferably have about 8 to about 20 or about 30 carbon atoms. It is preferred that the surfactant component be substantially free of ether groups, which may be particularly prone to interact with (and detrimentally effect) the chlorine dioxide precursor. A particularly useful sulfate-containing surfactant component is sodium dodecyl sulfate.

Specific examples of useful sulfonate-containing surfactant components include alkyl-containing sulfonates of alkali metals and alkaline earth metals. The alkyl groups of such salts can have about 8 to about 20 or about 30 or more carbon atoms. Such components may also include one or more aromatic hydrocarbon oxide groups, such as phenyloxide groups, without substantially detrimentally affecting the surfactant's stability. A particularly useful sulfonate-containing surfactant component is disodium alkyl diphenyloxide disulfonate.

The alkyl groups of the presently useful alkyl polyglucoside surfactant components preferably have about 8 to about 20 or about 30 carbon atoms. A particularly useful alkyl polyglucoside surfactant component is decyl polyglucoside.

In general, the surfactant component is effective to reduce the surface tension of the liquid medium in which it is contained (relative to the liquid medium without the surfactant component). The specific concentration of surfactant component in the present compositions depends on a number of factors, for example, the specific surfactant component being employed, the identity and concentration of other components present in the composition and the like. The concentration of surfactant component may be in the range of about 0.01% by weight or less to about 1% or about 5% by weight or more. Care should be taken to avoid using excessive amounts of surfactant component since this is wasteful and/or can have a detrimental effect on the contact lens being cared for or on the wearer of the contact lens. The surfactant component is preferably soluble in the present compositions, which are preferably solutions.

The enzyme or enzymes used are capable of removing at least one type of deposit material from a contact lens. The amount of such enzyme or enzymes used is preferably effective to remove substantially all of at least one type of deposit material from a deposit material laden contact lens in a reasonable time, preferably within about 12 hours, for example, in the range of about 1 minute to about 12 hours, and more preferably within about 2 hours, for example, about 1 minute to about 2 hours. The active enzyme-containing liquid medium preferably contains sufficient enzyme to provide between about 0.0001 to about 5 Anson units of activity, more preferably between about 0.001 or about 0.01 to about 0.1 or about 1 Anson unit, per single lens treatment. Higher or lower amounts may be used.

The enzyme employed may be selected from enzymes which are conventionally employed in the enzymatic cleaning of contact lenses. For example, many of the enzymes disclosed in Huth et al Reissue U.S. Pat. No. 32,672 and Karageozian et al U.S. Pat. No. 3,910,296 are useful in the present invention. Each of these patents is incorporated in its entirety herein by reference. Among the useful enzymes are those selected from proteolytic enzymes, lipases and mixtures thereof. The enzyme may be one or more carbohydrate-active or carbolytic enzymes. Specific examples of useful enzymes include proteases, amylases, lipases and mixtures thereof.

Preferred proteolytic enzymes are those which are substantially free of sulfhydryl groups or disulfide bonds. Metallo-proteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Aspergillus molds. Within this grouping, the still more preferred enzymes are the derived alkaline proteases generically called subtilisin enzymes. Reference is made to Deayl, L., Moser, P. W. and Wildi, B. S., "Proteases of the Genus Bacillus. II Alkaline Proteases", Biotechnology and Bioengineering, Vol. XII, pp. 213–249 (1970) and Keay, L. and Moser, P. W., "Differentiation of Alkaline Proteases from Bacillus Species" Biochemical and Biophysical Research Comm., Vol. 34, No. 5, pp. 600–604 (1969).

The Subtilisin enzymes are broken down into two sub-classes, subtilisin A and subtilisin B. In the subtilisin A grouping are enzymes derived from such species are *B. subtilis, B. licheniformis* and *B. pumilis*. Organisms in this subclass produce little or no neutral protease or amylase. The subtilisin B. sub-class is made up of enzymes from such organisms a *B. subtilis, B. subtilis var. amylosacchariticus, B. amyloliguefaciens* and *B. subtilis* NRRL B3411. these organisms produce neutral proteases and amylases on a level about comparable to their alkaline protease production. One or more enzymes from the subtilisin A sub-class are particularly useful.

In addition, other preferred enzymes are, for example, pancreatin, trypsin, collagenase, keratenase, carboxylase, aminopeptidase, elastase, and aspergillopeptidase A and B, pronase E (from *S. griseus*) and dispase (from *Bacillus polymyxa*).

An effective amount of enzyme is to be used in the practice of this invention. Such amount will be that amount which effects removal in a reasonable time (for example overnight) of substantially all of at least one type of deposit material from a lens deposited due to normal wear. This standard is stated with reference to contact lens wearers with a history of normal pattern of lens deposit material accretion, not the very small group who may at one time or another have a significantly increased rate of deposit material accretion such that cleaning is recommended every day, or every two or three days.

The amount of enzyme required to make an effective lens cleaner will depend on several factors, including the inherent activity of the enzyme.

Enzyme activity is pH dependent so for any given enzyme, there is a particular pH range in which that enzyme will function best. The determination of such range can readily be done by know techniques.

It has been found that many of the effective lens cleaning enzymes, such as described elsewhere herein, are inactivated in the presence of disinfecting amounts of chlorine dioxide.

To reduce or even eliminate this concern, in a particularly useful embodiment the enzyme can be present in a delayed release form together with a chlorine dioxide destroying component, preferably a chlorine dioxide reducing component or agent, such as described elsewhere herein, in an amount effective to chemically reduce substantially all the chlorine dioxide in a liquid medium. In this embodiment, the enzyme is released after the lens is disinfected. Thus, the enzyme is released at substantially the same time or after the chlorine dioxide destroying component and acts to clean the disinfected lens, with no substantially interference from chlorine dioxide.

The disinfecting and cleaning contacting preferably occur at a temperature to maintain the liquid medium substantially liquid. For example, when the liquid medium is aqueous-based, it is preferred that the contacting temperature be in the range of about 0° C. to about 100° C., and more preferably in the range of about 10° C. to about 60° C. Contacting at or about ambient temperature is very convenient and useful. The contacting preferably occur at or about atmospheric pressure. The disinfecting contacting preferably occurs for a time to substantially completely disinfect the lens being treated. Such contacting times can be in the range of about 0.1 hours to about 12 hours or more. The cleaning contacting preferably occurs for a time to substantially clean the lens of at least one type of deposit material, e.g., in the range of about 0.2 hours to about 12 hours or more.

In another embodiment, the activator component is included in the composition in a substantially inactive form and/or is released on a delayed release basis. For example, the enzyme and activator component can be present together in a single item, i.e., a layered tablet, pill or the like. After the item is introduced in the liquid medium containing the chlorine dioxide precursor, the enzyme first becomes available to remove deposit material from the to-be-cleaned lens. At this time, i.e., when the enzyme is cleaning the lens, the activator component remains in the item, effectively out of contact with the chlorine dioxide precursor. After a period of time, e.g., a predetermined period of time for which the item is designed, the activator component is released in the liquid medium. This causes chlorine dioxide formation which, in turn, results in disinfecting the lens in the liquid medium.

Tablets, pills, granules or the like which release their ingredients in a sequential, time delayed manner are well known and can be produced using conventional technology. Therefore, a detailed description of such items and such production technology is not presented here. However, such tablets, pills, granules or the like are preferably designed to allow one component sufficient time to perform its function before releasing another component which may interfere with the functioning of the first component. For example, if the item contains both an enzyme and an activator component, the item is preferably designed to allow the enzyme sufficient time to remove at least a major amount, and more preferably substantially all, of at least one type of deposit material, for example, protein-based deposit material, from the lens in the liquid medium. In other words, such items are preferably designed so that sufficient time elapses between release of the enzyme and release of the activator component to allow the enzyme to perform its cleaning function. Such sufficient time is preferably in the range of about one minute to about 2 hours, more preferably about five minutes to about one hour.

Although multi-layered (including core and coating layers) tablets or pills are preferred, the delayed release form of the present compositions can be present in any other suitable item or items, such as masses of powders, granules and the like. Delayed release technology is well known in the art as exemplified by the text *Controlled Drug Delivery*, 2nd Ed., Joseph R. Robinson & Vincent H. L. Lee, Eds., Marcel Dekker, Inc., New York, 1987.

Any suitable delayed release component or combination of delayed release components may be employed, provided that such component or components function as described herein and have no substantially detrimental effect on the other components present, on the lens being treated and on the human wearing the treated lens. The delayed release component is preferably at least partially, more preferably completely, water soluble. The delayed release component preferably comprises a major amount of at least one polymeric material.

In order to insure that the pH of the precursor aqueous liquid medium is maintained within the desired range, the aqueous liquid medium may include at least one buffer component. Although any suitable buffer component may be employed, it is preferred to select such component so as not to substantially detrimentally affect the chlorine dioxide. It is preferred that the buffer component be inorganic. Alkali metal and alkaline earth metal buffer components are advantageously used in the present invention.

Further, in order to avoid possible eye irritation, it is preferred that the presently useful liquid media have an osmolality (a measure of tonicity) of at least about 200 mOsmol/kg, preferably in the range of about 200 to about 350 or about 400 mOsmol/kg. In an especially useful embodiment, the osmolality or tonicity of the liquid medium substantially corresponds to the tonicity of the fluids of the eye, in particularly the human eye.

Any suitable ophthalmically acceptable tonicity component or components may be employed, provided that such component or components are compatible with the other ingredients of the precursor liquid medium and do not have deleterious or toxic properties which could harm the eye. Examples of useful tonicity components include sodium chloride, potassium chloride, mannitol, dextrose, glycerin, propylene glycol and mixtures thereof. In one embodiment, the tonicity component is selected from inorganic salts and mixtures thereof.

The amount of ophthalmically acceptable tonicity component utilized can vary widely. In one embodiment, the tonicity component is preferably present in the liquid medium in an amount in the range of about 0.5 to about 0.9 weight/volume percent of the formulation.

Typical of ophthalmically acceptable inorganic salt tonicity components are alkali metal chlorides and alkaline earth metal chlorides, such as sodium chloride, potassium chloride, calcium chloride and magnesium chloride.

One or more additional components can be included in the present useful liquid media. Such addition component or components are chosen to impart or provide at least one beneficial or desired property to the liquid media. Such additional components may be selected from components which are conventionally used in one or more contact lens care compositions. Examples of such additional components include cleaning agents, wetting agents, nutrient agents, sequestering agents, viscosity builders, contact lens conditioning agents, antioxidants, and the like. These addition components may each be included in the liquid medium in an amount effective to impart or provide the beneficial or desired property to the liquid medium. For example, such additional components may be included in the presently useful liquid media in amounts similar to the amounts of such components used in other, e.g., conventional, contact lens care products.

Examples of useful sequestering agents include disodium ethylene diamine tetraacetate, alkali metal hexametaphosphate, citric acid, sodium citrate and mixtures thereof.

Examples of useful viscosity builders include hydroxyethyl cellulose, hydroxymethyl cellulose, polyvinyl pyrrolidone, polyvinyl alcohol and mixtures thereof.

Examples of useful antioxidants include sodium metabisulfite, sodium thiosulfate, N-acetylcysteine, butylated hydroxyanisole, butylated hydroxytoluene and mixtures thereof.

The following non-limiting examples illustrate certain aspects of the present invention.

EXAMPLES 1 TO 3

The following tests were performed to determine the effects of carboxymethylcellulose on contact lens deposit formation during chlorine dioxide disinfection.

Conventional low water content hydrogel contact lenses made from polyhydroxyethyl methacrylate (poly HEMA) were selected for testing.

Each of the lenses was repeatedly subjected to the following cyclic processing. The lens was soaked for eight (8) hours in 10 ml of a lysozyme-containing artificial tear formulation (with periodic shaking) at room temperature. Thereafter, the lens was soaked for sixteen (16) hours in 10 ml of a disinfecting solution (described below) at pH 7.4 and room temperature. The lens was inspected under 7× magnification (microscope) for deposits. Two (2) contact lenses were tested using each disinfecting solution.

The disinfecting solutions were as follows:

Solution A: buffered saline containing 120 ppm of a stabilized chlorine dioxide product (sold by Bio-Cide International, Inc., under the trademark PUROGENE®).

Solution B: buffered saline containing about 120 ppm of the above-noted stabilized chlorine dioxide product, 200 ppm of sorbitol and 0.2% (w/v) of sodium carboxymethylcellulose.

Solution C: Same as Solution B and including 0.1% (w/v) of an ethylene oxide/propylene oxide block co-polymer-containing product sold by BASF under the trademark Pluronic F-68.

All the solutions had viscosities of less than 20 cps at 25° C.

A commercially available platinum-containing disc was included in each portion of the solutions used to promote the generation of chlorine dioxide from the stabilized chlorine dioxide product. The disc was replaced periodically to insure that a disinfecting amount of chlorine dioxide was always generated.

Results of these tests were as follows:

| Example | Solution | No. of Cycles | Comments |
| --- | --- | --- | --- |
| 1 | A | 29 | a, g |
| 2 | B | 91 | b, d, e, f, h, j |
| 3 | C | 91 | b, c, d, e, h, i | a. Deposits were observed under 7× scope after 5 to 7 cycles.
b. Deposits were not observed under 7× scope after 7 cycles.
c. Effects of the Pluronic F-86 were not noted in these experiments.
d. Deposits remained very light at 37 cycles. A conventional daily enzymatic contact lens cleaning formulation was effective to remove most deposits. Lenses did not look as clean as new but deposits were minimal at 48 cycles.
e. Sorbitol was eliminated after 37 cycles but pH was kept at 7.4 and sodium chlorite at 180 ppm was used in place of the stabilized chlorine dioxide product.
f. One lens looked hazy while the other was fine after 65 cycles. Both lenses showed haziness after 88 cycles.
g. Deposits were heavy after 29 cycles and the cycling was terminated.
h. New platinum-containing discs were used after 29 and 62 cycles.
i. Lenses looked clean after 91 cycles.
j. The lenses were subjected to conventional enzymatic cleaning which was effective in cleaning up the lenses, although some hazy spots remained.

a. Deposits were observed under 7× scope after 5 to 7 cycles.
b. Deposits were not observed under 7× scope after 7 cycles.
c. Effects of the Pluronic F-86 were not noted in these experiments.
d. Deposits remained very light at 37 cycles. A conventional daily enzymatic contact lens cleaning formulation was effective to remove most deposits. Lenses did not look as clean as new but deposits were minimal at 48 cycles.
e. Sorbitol was eliminated after 37 cycles but pH was kept at 7.4 and sodium chlorite at 180 ppm was used in place of the stabilized chlorine dioxide product.
f. One lens looked hazy while the other was fine after 65 cycles. Both lenses showed haziness after 88 cycles.
g. Deposits were heavy after 29 cycles and the cycling was terminated.
h. New platinum-containing discs were used after 29 and 62 cycles.
i. Lenses looked clean after 91 cycles.
j. The lenses were subjected to conventional enzymatic cleaning which was effective in cleaning up the lenses, although some hazy spots remained.

These results demonstrated that carboxymethylcellulose at 0.2% (w/v) delayed contact lens deposit formation in vitro effectively. Some protein deposits occurred after many cycles but could be handled by conventional cleaning enzyme formulations. In contrast, the heavy deposits formed on the contact lenses disinfected with Solution A could not be effectively removed with such conventional cleaning enzyme formulations. The effect of the surfactant, Pluronic F-68, was not apparent.

EXAMPLES 4 TO 6

Two types of hydrogel contact lenses were selected for testing. These lenses were as follows:

TYPE I—conventional low water content hydrogel contact lenses made from polyhydroxyethyl methacrylate (poly HEMA).

TYPE II—contact lenses made of an ionic, high water content hydrogel material.

These lenses were repeatedly subjected to the cyclic processing as described in Examples 1 to 3 except that the soaking in the artificial tear formulation occurred at 37° C. and without shaking.

The disinfecting solutions were as follows:

Solution D: buffered saline containing 120 ppm of the stabilized chlorine dioxide product described in Example 1 to 3 (or 180 ppm of sodium chlorite) at a pH of 7.4.

Solution E: buffered saline containing 120 ppm of the stabilized chlorine dioxide product described in Examples 1 to 3 and 0.2% (w/v) of sodium carboxymethylcellulose. The solution had a viscosity of between about 20 and about 100 cps at 25° C.

Solution F: same as Solution E except that different sodium carboxymethylcellulose was used and the solution had a viscosity of about 20 cps at 25° C.

A commercially available platinum-containing disc was included in each portion of the solutions used to promote the generation of chlorine dioxide from the precursor present in the solution. The disc was replaced periodically to insure that a disinfecting amount of chlorine dioxide was always generated.

Results of these tests were as follows:

| Example | Lens Type | Solution | No. of Cycles | Comments |
| --- | --- | --- | --- | --- |
| 4 | I | D | 31 | a, f, i |
| 4 | II | D | 55 | b |
| 5 | I | E | 59 | e, j |
| 5 | II | E | 59 | c, d |
| 6 | I | F | 59 | e, g, h |
| 6 | II | F | 59 | c, d | a. Deposits were initially observed under 7× magnification after 8 cycles. Lenses were heavily covered after 31 cycles. Rubbing with cleaner can only improve a little.
b. Discoloration was observed after 3 cycles. Deposits remained light after 55 cycles.
c. Lenses remained clean
d. No discoloration to the naked eye.
e. Some spots of deposits were found at 24–27 cycles and were effectively removed, by rubbing with a cleaner. Deposits remain very light after 55 cycles.
f. Rubbing and rinsing with cleaner can not remove the heavy deposit layer after 55 cycles.
g. One lens was lost physically.
h. The remaining lens had some hazy area and was treated with conventional enzymatic cleaning formulation after 59 cycles, but only marginal improvement was observed.
i. One lens was treated with conventional enzymatic cleaning formulation after 59 cycles but deposits remained heavy.
j. Lenses were cleaned with conventional enzymatic cleaning formulation after 59 cycles. Some tiny spots of deposits remained.

a. Deposits were initially observed under 7× magnification after 8 cycles. Lenses were heavily covered after 31 cycles. Rubbing with cleaner can only improve a little.

b. Discoloration was observed after 3 cycles. Deposits remained light after 55 cycles.

c. Lenses remained clean d. No discoloration to the naked eye.

e. Some spots of deposits were found at 24–27 cycles and were effectively removed by rubbing with a cleaner. Deposits remain very light after 55 cycles.

f. Rubbing and rinsing with cleaner can not remove the heavy deposit layer after 55 cycles.

g. One lens was lost physically.

h. The remaining lens had some hazy area and was treated with conventional enzymatic cleaning formulation after 59 cycles, but only marginal improvement was observed.

i. One lens was treated with conventional enzymatic cleaning formulation after 59 cycles but deposits remained heavy.

j. Lenses were cleaned with conventional enzymatic cleaning formulation after 59 cycles. Some tiny spots of deposits remained.

Deposits on the TYPE I lenses were more severe when the lenses were soaked in artificial tear at 37° C. rather than at room temperature (as in examples 1 to 3). Lenses were heavily covered by deposits and became opaque. Conventional enzymatic cleaning formulation showed little effectiveness to remove or reduce the deposits. Some spots of deposits were also found on lenses disinfected with the sodium carboxymethylcellulose system after many cycles. But simple rubbing and rinsing or conventional enzymatic cleaning formulations can be used to effectively clean these lenses.

Discoloration was observed with the TYPE II lenses disinfected with chlorine dioxide without sodium carboxymethylcellulose. Deposits were found on these TYPE II lenses. However, the deposits were lighter than those on the other lenses and occurred only after more cycles. Very little deposit material was found on the TYPE II lenses disinfected with the carboxymethylcellulose-containing system.

Carboxymethylcellulose of different viscosity grades were used. The low viscosity material did generally as well as the medium viscosity material in delaying deposit formation and preventing discoloration for either the TYPE I or TYPE II lenses.

EXAMPLE 7

The following solution is prepared by blending the various components together and has the following composition:

| | |
| --- | --- |
| Sodium chloride | 0.73% (w/v) |
| Boric acid | 0.20% (w/v) |
| Stabilized Chlorine Dioxide[1] | 0.0178% (w/v) |
| Sodium Carboxymethylcellulose | 0.2% (w/v) |
| pH | 7.4 |
| U.S.P. water | Q.S. |

[1]Stabilized chlorine dioxide product identified in Examples 1 to 3

(1) Stabilized chlorine dioxide product identified in Examples 1 to 3

A 1000 ml quantity of this solution is packaged in a container suitable for dispensing 10 ml portions of the solution into a lens container. The solution container includes a tip portion which includes particles of palladium/gold-containing silica gel. As the solution passes through the tip into the lens container, the chlorine dioxide in the solution is activated to form chlorine dioxide in sufficient quantities to disinfect a contact lens located in the lens container. Such solution containers are more fully described in Mitchell et al U.S. Pat. No. 5,197,636 which is incorporated in its entirety herein by reference.

When it is desired to disinfect a contact lens, it is placed in a conventional lens container suitable for storing the lens. A 10 ml quantity of the solution from the solution container is passed through the tip portion and into the lens container. After one hour, the lens is removed from the lens container, rinsed with a buffered saline solution and placed directly in the eye. It is found that the treated contact lens is disinfected and is suitable for safe and comfortable wear in the eye.

The solution in the solution container is found to remain sufficiently stable to produce a contact lens disinfecting amount of chlorine dioxide for use as described above for a period of two months from the time the solution is initially used as described above. The presence of the sodium carboxymethylcellulose is effective to prevent or at least delay the formation of deposit material on the contact lens during the disinfecting contacting.

While this invention has been described with respect to various specific examples and embodiments, it is to be understood that the invention is not limited thereto and that it can be variously practiced with the scope of the following claims.

What is claimed is:

1. A composition comprising:
    a liquid medium;
    chlorine dioxide precursor in said liquid medium in an amount effective, when activated in said liquid medium, to form a chlorine dioxide-containing composition including a contact lens disinfecting amount of chlorine dioxide; and a polyanionic component in said liquid medium in an amount effective, in the chlorine dioxide-containing composition, to reduce the amount of proteinaceous deposit material on a contact lens immersed in the chlorine dioxide-containing composition, provided that said polyanionic component and any precursor thereof do not act to substantially delay the release of another component in the chlorine dioxide-containing composition and any liquid-containing precursor thereof, said polyanionic component comprises a polymeric material having multiple anionic charges, and said composition having a viscosity of less than 50 cps at 25° C.

2. The composition of claim 1 wherein said liquid medium comprises water, and said polyanionic component is water soluble.

3. The composition of claim 1 wherein said polyanionic component is effective to reduce the amount of proteinaceous deposit material on a contact lens immersed in the chlorine dioxide-containing composition compared to the amount of proteinaceous deposit material on a contact lens immersed in a similar chlorine dioxide-containing composition without said polyanionic component.

4. The composition of claim 1 wherein said polyanionic component is selected from the group consisting of anionic cellulose derivatives, anionic polymers derived from acrylic acid, anionic polymers derived from methacrylic acid, anionic polymers derived from alginic acid, anionic polymers derived from amino acids and mixtures thereof.

5. The composition of claim 1 wherein said polyanionic component comprises an anionic cellulose derivative.

6. The composition of claim 1 wherein said polyanionic component comprises a carboxymethylcellulose.

7. The composition of claim 1 which further comprises an activator component in an amount effective when released in a liquid medium containing said chlorine dioxide precursor to result in formation of a contact lens disinfecting amount of chlorine dioxide from said chlorine dioxide precursor in the liquid medium.

8. The composition of claim 1 which further comprises an enzyme component in an amount effective to remove proteinaceous deposit material from said contact lens.

9. The composition of claim 7 which further comprises an enzyme component in an amount effective to remove proteinaceous deposit material from said contact lens.

10. The composition of claim 9 wherein said activator component and said enzyme component are each a component of a formulation structured to release said enzyme component in a liquid medium containing said chlorine dioxide precursor prior to releasing said activator component in the liquid medium.

11. A method for reducing the amount of proteinaceous deposit material during disinfection of a contact lens which comprises:

contacting a contact lens with a composition comprising a liquid medium containing chlorine dioxide in an amount effective to disinfect said contact lens, and a polyanionic component in said liquid medium in an amount effective to reduce the amount of proteinaceous deposit material on said contact lens, provided that said polyanionic component and any precursor thereof do not act to substantially delay the release of another component in said liquid medium and any liquid-containing precursor thereof, said polyanionic component comprises a polymeric material having multiple anionic charges, and said composition having a viscosity of less than 50 cps at 25° C.

12. The method of claim 11 wherein said liquid medium comprises water, and said polyanionic component is water soluble.

13. The method of claim 11 wherein said polyanionic component is effective to reduce the amount of proteinaceous deposit material on said contact lens compared to the amount of proteinaceous deposit material on a contact lens contacted with a similar liquid medium without said polyanionic component.

14. The method of claim 11 wherein said polyanionic component is selected from the group consisting of anionic cellulose derivatives, anionic polymers derived from acrylic acid, anionic polymers derived from methacrylic acid, anionic polymers of alginic acid, anionic polymers of amino acids and mixtures thereof.

15. The method of claim 11 wherein said polyanionic component comprises an anionic cellulose derivative.

16. The method of claim 11 which further comprises contacting said contact lens with an enzyme component in an amount effective to remove proteinaceous deposit material from said contact lens.

* * * * *